United States Patent [19]

Johnson et al.

[11] 4,427,575
[45] Jan. 24, 1984

[54] CATALYST

[75] Inventors: Marvin M. Johnson; Gerhard P. Nowack; Simon Kukes, all of Bartlesville, Okla.

[73] Assignee: Phillips Petroleum Company, Bartlesville, Okla.

[21] Appl. No.: 488,881

[22] Filed: Apr. 26, 1983

Related U.S. Application Data

[62] Division of Ser. No. 395,939, Jul. 7, 1982.

[51] Int. Cl.³ .............................................. B01J 27/14
[52] U.S. Cl. ...................................... 502/208; 502/210
[58] Field of Search .................................. 252/435, 437

[56] References Cited

U.S. PATENT DOCUMENTS

| | | | |
|---|---|---|---|
| 2,349,243 | 5/1944 | Bates | 196/52 |
| 2,656,323 | 10/1953 | Bielawski et al. | 252/435 |
| 2,921,103 | 1/1960 | Pitzer | 585/670 |
| 2,945,015 | 7/1960 | Detter | 252/435 X |
| 3,179,580 | 4/1965 | Fukui et al. | 252/428 |
| 3,217,059 | 11/1965 | Hervert et al. | 585/670 |
| 3,310,598 | 3/1967 | Noddings et al. | 585/667 |
| 3,475,511 | 10/1969 | Manning | 585/666 |
| 3,527,833 | 9/1970 | Kehl | 585/670 |
| 3,527,834 | 9/1970 | Kehl | 585/670 |
| 3,584,070 | 6/1971 | Reiger | 585/671 |
| 3,642,933 | 2/1972 | Heckelsberg | 585/670 |
| 3,663,453 | 5/1972 | Myers | 585/671 |
| 3,730,958 | 5/1973 | Myers | 585/671 |
| 3,905,914 | 9/1975 | Jurewicz et al. | 252/435 X |
| 4,059,679 | 11/1977 | Clearfield | 252/437 |

FOREIGN PATENT DOCUMENTS 57-42637  3/1982  Japan .................................. 252/437

Primary Examiner—William G. Wright

[57] ABSTRACT

A catalyst comprising essentially zirconium phosphate and at least one of chromium and thorium.

4 Claims, No Drawings

CATALYST

This is a division application of our copending application having Ser. No,. 395,939, filed July 7, 1982.

The invention relates to the selective isomerization of an aliphatic mono-olefin. In accordance with another aspect, this invention relates to the selective isomerization of an aliphatic mono-olefin having an internal double bond to produce and to improve yield of the corresponding terminal olefin. A further aspect of this invention relates to a catalyst for isomerizing aliphatic mono-olefins.

BACKGROUND OF THE INVENTION

Terminal olefins, also called 1-olefins or alpha-olefins, are useful as reactants for a number of commercially important processes such as hydro-formylation, sulfonation, alkylation and acid oligomerization. In these processes they are more reactive than internal olefins. The homologous series of 1-olefins can be prepared by the thermal cracking of paraffinic hydrocarbons. However, olefins produced by catalytic cracking will generally have close to thermodynamic equilibrium composition determined by the cracking temperature for the mixture of normal and branched isomers. These isomers are frequently not easily separated. When the normal and branched isomers can be separated from each other as with butenes, then the normal olefins can be treated by the catalyst of this invention to provide a fraction that is enriched in 1-olefins.

Accordingly, an object of this invention is to provide a process for the shifting of an internal double bond in an aliphatic mono-olefin hydrocarbon to the terminal position.

Another object of this invention is to provide a catalytic process for shifting an internal bond in an aliphatic mono-olefin to the 1- or terminal position.

Another object of this invention is to provide a catalytic process for the selective isomerization or shifting of an internal unsaturation or double bond in an aliphatic mono-olefin to a terminal or 1-position.

Other aspects, objects as well as the several advantages of the invention are apparent from a study of this disclosure and the appended claims.

SUMMARY OF INVENTION

According to the present invention, the double bond of an aliphatic mono-olefin is shifted from an internal position to a terminal position by contacting said mono-olefin under isomerization conditions with an amorphous catalyst zirconium phosphate and at least one of chromium and thorium.

In accordance with a specific embodiment of the invention, the hydrocarbon feed stream containing internally unsaturated mono-olefins, such as butene-2, is subjected to isomerization conditions in the presence of a catalyst comprising zirconium phosphate and at least one of chromium and thorium to effect double bond isomerization and form butene-1 from butene-2.

DETAILED DESCRIPTION

Aliphatic mono-olefins having more than three carbon atoms are amenable to treatment by the catalyst of this invention, including branched chain as well as normal chain compounds. With both, the equilibrium concentration of the 1-olefin isomer increases with increasing temperature. In general, olefins being treated will have between 4 and 20 carbon atoms.

Representative examples of such olefins include pentene-2, 2-methylbutene-2, hexene-2, hexene-3, 3-methylpentene-2, heptene-2, heptene-3, octene-2, octene-3, octene-4, and the like, as well as mixtures thereof.

Especially preferred as feedstock to be treated with the catalyst of the invention are the isomeric n-butenes.

The amorphous catalyst of this invention comprises zirconium phosphate and at least one of chromium and thorium. The catalyst composition can be prepared by combining a compound of chromium or thorium, preferably in solution with a zirconium compound and a material convertible to the phosphate. One preferred procedure for preparing the catalyst is to coprecipitate a mixture of zirconium and thorium or zirconcium and chromium. Typically a solution with desired metal ratios of a suitable zirconium compound and a suitable thorium or chromium compound is prepared. To this is added a solution containing a soluble source of phosphate, causing precipitation of a mixed metal phosphate composition. The precipitate is filtered, washed, then dried at 100-150° C. for 4-16 hours. Dried catalyst is activated by calcination at 400-800° C. in air, for about 30 minutes to 24 hours.

Another preferred procedure for preparing the catalyst is to impregnate zirconium phosphate with a thorium or chromium compound. Typically, this will be accomplished by employing the techinque of incipient wetness. Thus, a solution of a suitable thorium or chromium compound is prepared employing about 0.5-1 mL of liquid per gram of zirconium phosphate support to be treated. The solution is added to dry zirconium phosphate support which is allowed to take up the added solution. The wetted support is then dried at 100-150° for 4-16 hours, the calcined in air at 400-800° C. for about 30 minutes to 24 hours.

Suitable zirconium, thorium, and chromium compounds employed in the preparation of the inventive catalyst include compounds soluble in the solvent employed. Suitable solvents include polar solvents such as alcohols, nitriles and water. Water is preferred.

Compounds of zirconium which are applicable include the oxychlorides, halides, nitrates, sulfates, acetates, and the like, and mixtures thereof. Exemplary compounds include zirconyl chloride, zirconyl bromide, zirconyl iodide, zirconium tetrachloride, zirconium fluoride, zirconium nitrate, and the like.

Compounds of thorium which are applicable include the halides, nitrates, sulfates, acetates, oxalates, and the like, and mixtures thereof. Exemplary compounds include thorium bromide, thorium chloride, thorium iodide, thorium nitrate, thorium picrate, thorium sulfate, and the like.

Compounds of chromium which are applicable include the halides, nitrates, sulfates, acetates, oxychlorides, and the like. Exemplary compounds include chromium bromide, chromium acetate, chromium chloride, chromium hydroxide, chromium nitrate, chromium oxalate, chromium trioxide, chromium sulfate, and the like.

Compounds which act as a source of phosphate will be of the following general structure:

where n=0, 1, 2, 3 and M=Li, Na, K, $NH_4$, ... Exemplary compounds include sodium orthophosphate, dihydrogen sodium orthophosphate, monohydrogen sodium orthophosphate, ammonium orthophosphate, dihydrogen ammonium phospate, monohydrogen ammonium phosphate, phosphoric acid, and the like, and mixtures thereof.

The chromium and/or thorium incorporated in the catalyst along with zirconium phosphate will be in an amount sufficient to increase the activity and selectively of the catalyst with respect to the production of terminal olefins. In general, the amount of chromium present in the catalyst (calculated as wt. % metal) will range from 0.1 to about 20, preferably about 1.0 to about 15, and the amount of thorium present in the catalyst (calculated as wt. % metal) will range from 1.0 to about 50, preferably about 5.0 to about 40.0, and most preferably about 20.0 to about 40.0.

In carrying out the isomerization reaction with the catalyst of the invention, suitable reaction conditions or isomerization conditions can be used which effectively cause double bond isomerization of the olefins present in the feed. In general, the temperature at which isomerizationis effected with this catalyst is about 300–1100° F. Preferably the temperature will be in the range of about 500–900° F. Reaction pressure can vary appreciably and can be subatmospheric and preferably will not exceed about 500 psig to avoid condensation reactions that ultimately lead to excessive coke formation on the catalyst.

Contact time of reactants on the catalyst expressed as liquid hourly space velocity (LHSV) can range between about 0.5 and 20. Preferably, LHSV will be between about 1 and 5.

EXAMPLE I

Catalyst Preparation

Catalyst A was prepared by adding a solution of 54.0 g (0.409 moles of $(NH_4)_2HPO_4$ in 400 mL water to a solution of 25 g (~0.100 moles) $ZrO(NO_3)_2.4H_2O$ dissolved in one liter of water. After being stirred for 5 minutes, the recipitate was removed by filtration, washed with 1.5 mL of hot water, dried in an oven and finally calcined in air for 5 hours at 550° C. The catalyst contained by analysis 42.7 wt. % Zr and 13.0 wt. % P, had 141 $m^2/g$ surface area, and 0.437 mL/g pore volume.

Catalyst B was prepared by adding a solution of 52.8 g (0.40 moles) of $(NH_4)_2HPO_4$ in 400 mL of water to 124 g (0.50 moles) of $Cr(C_2H_3O_2)_3.H_2O$ in 500 mL of water. There was no apparent reaction until the solution, upon being heated, formed a gel at 198° F. It was diluted with 100 mL of 1.5 M $NH_4OH$ but the precipitated gel remained unfilterable. Solvent was removed in a drying oven at 100° C, then the solid product was calcined in air for 2 hours at 482° C. to produce a friable material weighing 69 g. It was not further characterized.

Catalyst C was prepared by adding a solution of 30 g (0.227 moles) of $(NH_4)_2HPO_4$ in 300 mL of water to a solution of 41 g (0.102 moles) $Cr(NO_3)_3.9H_2O$ and 30 g (~0.120 moles) of $ZrO(NO_3)_2.xH_2O$ in one liter of water. The resulting precipitate was filtered, washed with one liter of hot water, dried overnite in an over at 140° C., then calcined in air for 5 hours at 550° C. The catalyst contained by analysis 15.8 wt. P, 13.5 wt. % Cr, and 27.1 wt. % Zr. Its surface area was 166 $m^2/g$, with 0.86 mL/g pore volume.

Catalyst D was prepared by adding a solution of 4 g (0.010 moles) $Cr(NO_3)_3.9H_2O$ in 12 mL of water to 20 g of catalyst A, then drying overnite at 140° C. and finally calcining for 4 hours at 600° C. The finished catalyst containing 2.50 wt. % Cr by calculation.

Catalyst C and D were analyzed by x-ray diffraction and determined to be amorphous.

Catalyst E was prepared by adding a solution of 26.6 g (0.201 moles) of $(NH_4)_2HPO_4$ in 250 mL of water to a solution of 23 g (0.092 moles) of $Zro(NO_3)_2.xH_2O$ and 52.5 g (0.095 moles) of $Th(NO_3)_4.4H_2O$ in 700 mL of water. The precipitate was filtered, washed with water, dried in an oven, and finally calcined for 3 hours at 550° C. Chemical analyses were not made, but the catalyst was found by x-ray diffraction analysis to be amorphous.

EXAMPLE II

Runs were made with catalysts A-E to isomerize Phillips Pure Grade butene-2. Catalyst (−15+45 mesh) was placed in a ⅜" i.d. stainless steel reactor and the butene passed downflow at about 2.0 LHSV and atmospheric pressure. Reaction temperature is indicated in the table. Gaseous products were analyzed by GLC. The table presents the results of a series of analyses made during the runs with each catalyst. Analyses from catalysts B, C and D were made on a different chromatograph than were catalysts A and E. Catalysts A and B, which are not part of this invention, exhibited appreciably lower selectivity for olefin isomerization than catalysts C, D and E did. In addition to the products shown in the table, catalyst A produced an appreciable volume of product that was liquid at room temperature. Inventive catalysts C, D and E yielded less propylene, and iso and normal butane than did catalysts A and B.

TABLE I

| Catalyst | A (Control) | B (Control) | C (Invention) | | D (Invention) | E (Invention) |
|---|---|---|---|---|---|---|
| No. of Samples | 10 | 3 | 2 | 4 | 4 | 3 |
| Temp, °C. | 316 | 316 | 371 | 316 | 371 | 371 | 316 |
| $CH_4$ | 0.003 | N.D. | N.D. | N.D. | N.D. | N.D. | N.D. |
| $C_2$'s | 0.010 | N.D. | N.D. | N.D. | N.D. | N.D. | 0.001 |
| $C_3H_8$ | N.D. | N.D. | N.D. | N.D. | N.D. | N.D. | N.D. |
| $C_3H_6$ | 0.42 | 0.22 | 0.52 | trace | trace | trace | 0.04 |
| i-$C_4H_{10}$ | 0.37 | 0.18 | 0.59 | N.D. | N.D. | N.D. | 0.07 |
| i-$C_4H_8$ | 18.1 | 20.3* | 27.6* | 15.5* | 19.3* | 19.0* | 12.1 |
| n-$C_4H_{10}$ | 0.67 | 0.50 | 1.57 | trace | 0.5 | trace | 0.29 |
| i-$C_4H_8$ | 1.69 | N.D. | N.D. | N.D. | N.D. | N.D. | 0.19 |
| c-2-$C_4H_8$ | 29.0 | 29.7 | 26.8 | 32.8 | 32.4 | 33.4 | 31.4 |
| t-2-$C_4H_8$ | 44.6 | 48.6 | 41.9 | 51.5 | 47.8 | 47.5 | 55.1 |
| $C_4H_6$ | N.D. | N.D. | N.D. | N.D. | N.D. | N.D. | N.D. |

TABLE I-continued

| Catalyst | A (Control) | B (Control) | | C (Invention) | | D (Invention) | E (Invention) |
|---|---|---|---|---|---|---|---|
| $C_5+$ | 5.12 | 0.48 | 0.92 | trace | trace | trace | 0.84 |

*Includes i-$C_4H_8$

We claim:

1. An amorphous catalyst composition comprising:
   (a) zirconium phosphate and at least one of
   (b) chromium, and
   (c) thorium.

2. A catalyst according to claim 1 wherein amounts of (b) and (c) present in the catalyst (calculated as wt. % metal) range from about 0.1 to about 20, and 1.0 to about 50, respectively.

3. A catalyst according to claim 1 which comprises zirconium phosphate and chromium.

4. A catalyst according to claim 1 which comprises zirconium phosphate and thorium.